United States Patent [19]
Ponsi et al.

[11] Patent Number: 6,024,217
[45] Date of Patent: Feb. 15, 2000

[54] DISPOSAL CONTAINER HAVING MULTIPLE POSITION CLOSURE

[76] Inventors: Lawrence G. Ponsi, 728 Longtree Dr., Wheeling, Ill. 60090; Paul H. Hanifl, 41 Sandalwood La., Barrington, Ill. 60010

[21] Appl. No.: 09/139,305

[22] Filed: Aug. 25, 1998

[51] Int. Cl.[7] .................................................. B65D 83/10
[52] U.S. Cl. .......................................... 206/370; 220/254
[58] Field of Search ................................... 206/366, 370; 220/254, 345.2, 345.4, 820, 821, 823, 824, 910

[56] References Cited

U.S. PATENT DOCUMENTS

| | | | |
|---|---|---|---|
| 3,164,286 | 1/1965 | Kole | 220/821 |
| 5,085,338 | 2/1992 | Inagaki | 220/254 |
| 5,507,408 | 4/1996 | Mosior et al. | 206/370 |
| 5,590,774 | 1/1997 | Roberts | 206/370 |

*Primary Examiner*—David T. Fidei
*Attorney, Agent, or Firm*—Lee, Mann, Smith, McWilliams, Sweeney & Ohlson

[57] ABSTRACT

A disposal container for retention of medical waste and the like. The container includes a container body with a separate lid appropriately affixed to the container body. An access aperture is provided in the lid, and the closure assembly is provided to overlie the access aperture in order to provide various degrees of opening or closure of the container. The closure assembly includes a rotary closure which is positionable in a series of positions to control access to the interior of the disposal container.

19 Claims, 5 Drawing Sheets

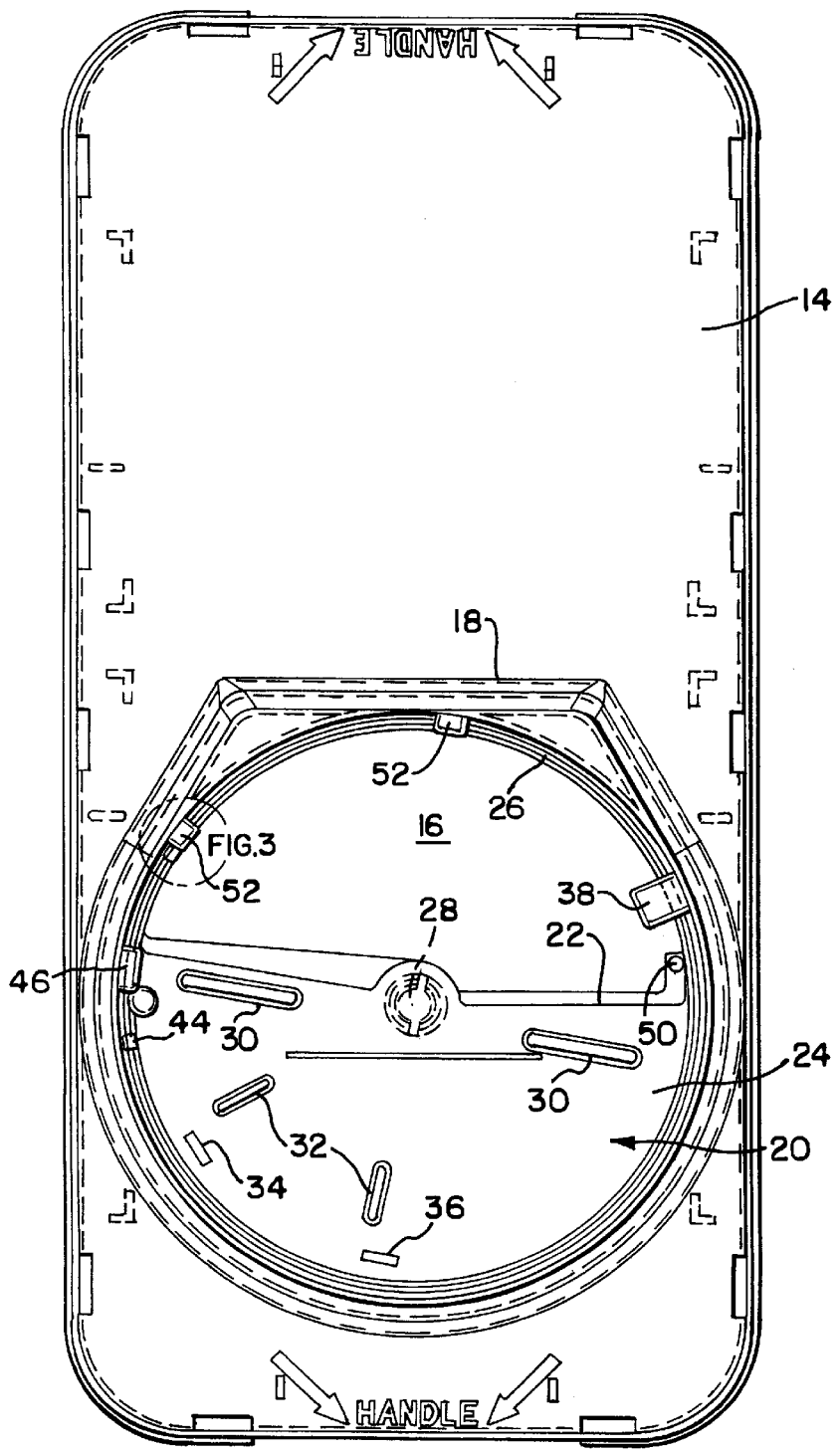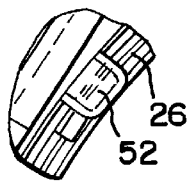

DISPOSAL CONTAINER HAVING MULTIPLE POSITION CLOSURE

BACKGROUND OF THE INVENTION

This invention relates to disposal containers, and in particular to a disposal container having a rotary closure which can be positioned at a series of positions to control access to the interior of the container.

Disposal containers, particularly when used in connection with disposal of biohazardous medical waste, need to have some means of controlling access to the interior of the container. Therefore, over the years, various types of containers have been developed to control access in some manner, from those containers that have limited openings with no closure, to those having some type of serpentine entry path, to those having a closure mechanism which can be positioned to control access to the interior of the container.

Often, it is desired to have a container which can be fully opened, but which also has some means of further restricting the opening, without closing it completely, in order to temporarily limit access to the interior of the container. This type of container is particularly advantageous when used in a home care environment, where the container is handled by an untrained person rather than a trained medical practitioner of some sort.

SUMMARY OF THE INVENTION

The invention is directed to a disposal container, which comprises a container body, a lid at the top of the container body, an access aperture in the lid, and a closure assembly which is shaped to overlie the access aperture. The closure assembly comprises a rotary closure having an open portion and a closed portion. Means is provided for positioning the rotary closure in an open position with the opened portion in registration with the aperture, thereby permitting full access to the aperture and the interior of the container body. Means is also provided for positioning the rotary closure in a locked position with the closed portion in registration with the aperture, thereby permanently preventing access to the aperture. Means is further provided for positioning the rotary closure in at least one intermediate position between the opened position and the locked position with the rotary closure being temporarily prevented, at the intermediate position, from rotation toward one of either the opened position or the locked position. Finally, means is provided for moving the rotary closure from the intermediate position by temporarily displacing a portion of the rotary closure relative to the lid in order to release the closure from the intermediate position.

In accordance with the preferred form of the invention, there are at least two of the intermediate positions, one of the intermediate positions comprising a partially opened positioned permitting limited access to the aperture, and the other of the intermediate positions comprising a temporarily closed position which temporarily prevents access to the aperture. In this form of the invention, the means for positioning the rotary closure at the partially opened position comprises a control tab in the lid which extends over the rotary closure and an upstanding nub on the rotary closure which is aligned to engage the control tab.

In accordance with the preferred form of the invention, the nub includes an inclined shoulder to permit rotation of the rotary closure in one direction with the nub passing beneath the control tab. The nub also includes a vertical wall, opposite the inclined shoulder, to prevent rotation of the closure past the control tab as the closure is rotated in the opposite direction.

At the temporarily closed position, means is provided for inhibiting rotation of the rotary closure to the locked position. That means comprises a first obstruction beneath the rotary closure which is engagable by a second obstruction formed in the lid. At least one of the obstructions can be frangible so that when broken or deformed, the closure can then be rotated to the locked position.

BRIEF DESCRIPTION OF THE DRAWINGS

The invention is described in greater detail in the following description of an example embodying the best mode of the invention, taken in conjunction with the drawing figures, in which:

FIG. 2 is an enlarged top plan view of the lid according to the invention, with the rotary closure shown in the opened position, FIG. 3 is a further enlarged partial top plan view of a fragmentary portion of FIG. 2.

DESCRIPTION OF AN EXAMPLE EMBODYING THE BEST MODE OF THE INVENTION

Figure 1:
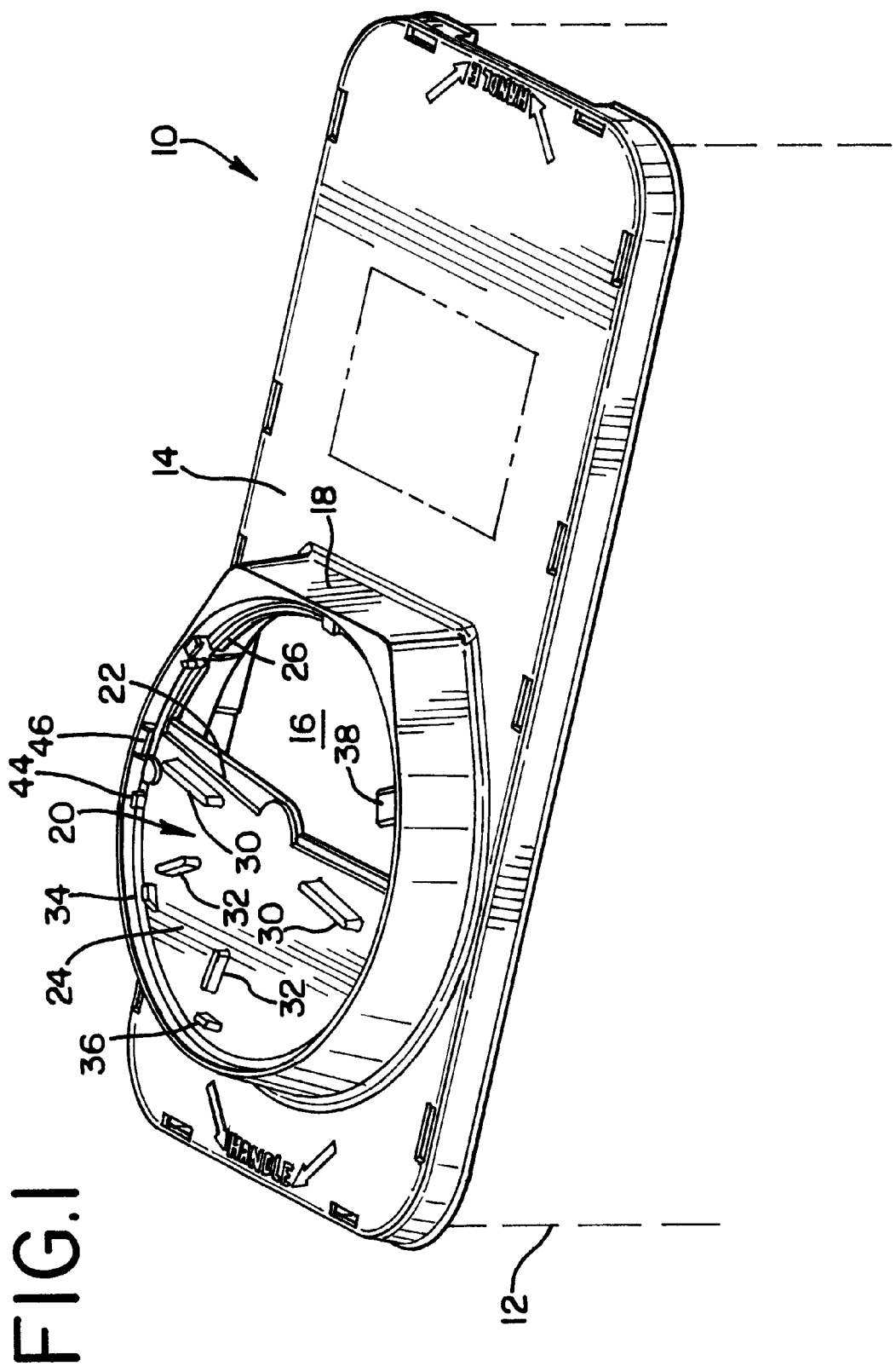
FIG. 1 is a perspective view of a disposal container according to the invention, with the lid and closure assembly shown in bold and the container body shown in phantom.

A disposal container according to the invention is depicted generally at ten in FIG. 1. The disposal container is preferably plastic or a similar material, and comprises two basic portions, a container body 12, shown only in phantom, and a lid 14 which is appropriately affixed to the top of the container body 12. The container body 12 can be of any size or shape, and is therefore not illustrated in detail. Also, the lid 14 can be affixed to the container body in any well-known fashion, and that means is therefore also not illustrated. While it is preferred that the lid 14 be a separate element applied to the container body 14, it is also possible to form the lid as an integral part of the container body.

As illustrated in the drawing figures, the lid 14 includes a single access aperture 16 therein, the access aperture 16 being located in an upstanding pedestal 18 extending upwardly from the top surface of the lid 14. The pedestal 18 facilitates utilization of the invention, but also can be omitted.

A closure assembly is provided to overlie the access aperture 16. The closure assembly is composed of a rotary closure 20 having two parts, an open portion 22 and a closed portion 24. As illustrated, the open portion 22 is shaped to be generally coterminal with the access aperture 16 when the rotary closure is in the opened position, as described in greater detail below. The open portion is defined generally between the closed portion 24 and an integral guide ring 26 which facilitates the rotary movement of the rotary closure 20. As is conventional, the rotary closure 20 includes a central axle 28 which extends through an appropriate hole in the lid 14 for purposes of rotation. Any type of axle can be utilized for rotation, from an integral extension from the closed portion 24 of the rotary closure 20 to a separate pin, bolt or other type of connection.

To facilitate rotating of the rotary closure 20 about the central axle 28, the rotary closure 20 includes a pair of oppositely situated grips 30. Subsidiary, some what smaller grips 32 can also be employed to facilitate rotation, as will become apparent from the further discussion below.

Figure 10:
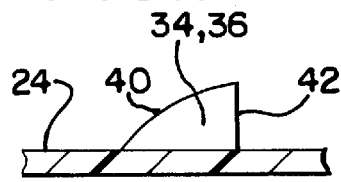
FIG. 10 is a side elevational illustration of the upstanding nubs according to the invention.

The closure 20 also includes a pair of upstanding nubs 34 and 36 which are aligned with and engage a control tab 38 in the lid 14 which extends over the rotary closure 20 as illustrated. As best shown in FIG. 10, each of the nubs 34 and 36 includes an inclined shoulder 40 leading from the top surface of the closed portion 24 to a vertical wall 42 extending generally perpendicular to the closed portion 24. The inclined shoulder 40 is shaped to pass beneath, and displace upwardly, the control tab 38 while the vertical wall 42 is shaped to butt against the control tab 38 to prevent rotation without displacement of either the tab 38 or the portion of the rotary closure 20 adjacent the nub 34 or 36.

The rotary closure 20 also includes an upstanding stop 44 shaped to engage both the control tab 38 and a shorter secondary tab 46 which also extends from the structure of the lid 14. Finally, an obstruction 48 is formed in the underside of the rotary closure 20 and is engagable with a second obstruction 50 formed in the lid 14. Preferably, at least the second obstruction 50 is frangible and can be deformed or displaced when the first obstruction 48 engages the second obstruction 50.

To guide the rotary movement of the rotary closure 20, a series of secondary mounting tabs 52 may be employed. As illustrated, the mounting tabs 52 extend from the lid 14, and are sufficiently short in extension so that they do not engage or interfere with the nubs 34 and 36 as the nubs pass.

In operation, the rotary closure 20 is in the opened position as illustrated in FIGS. 1 and 2. In that position, the open portion 22 is in registration with the access aperture 16. Also, the stop 44 is proximate the secondary tab 46 so that the rotary closure 20 cannot be rotated in the clockwise direction (in relation to FIG. 2).

Figure 4:
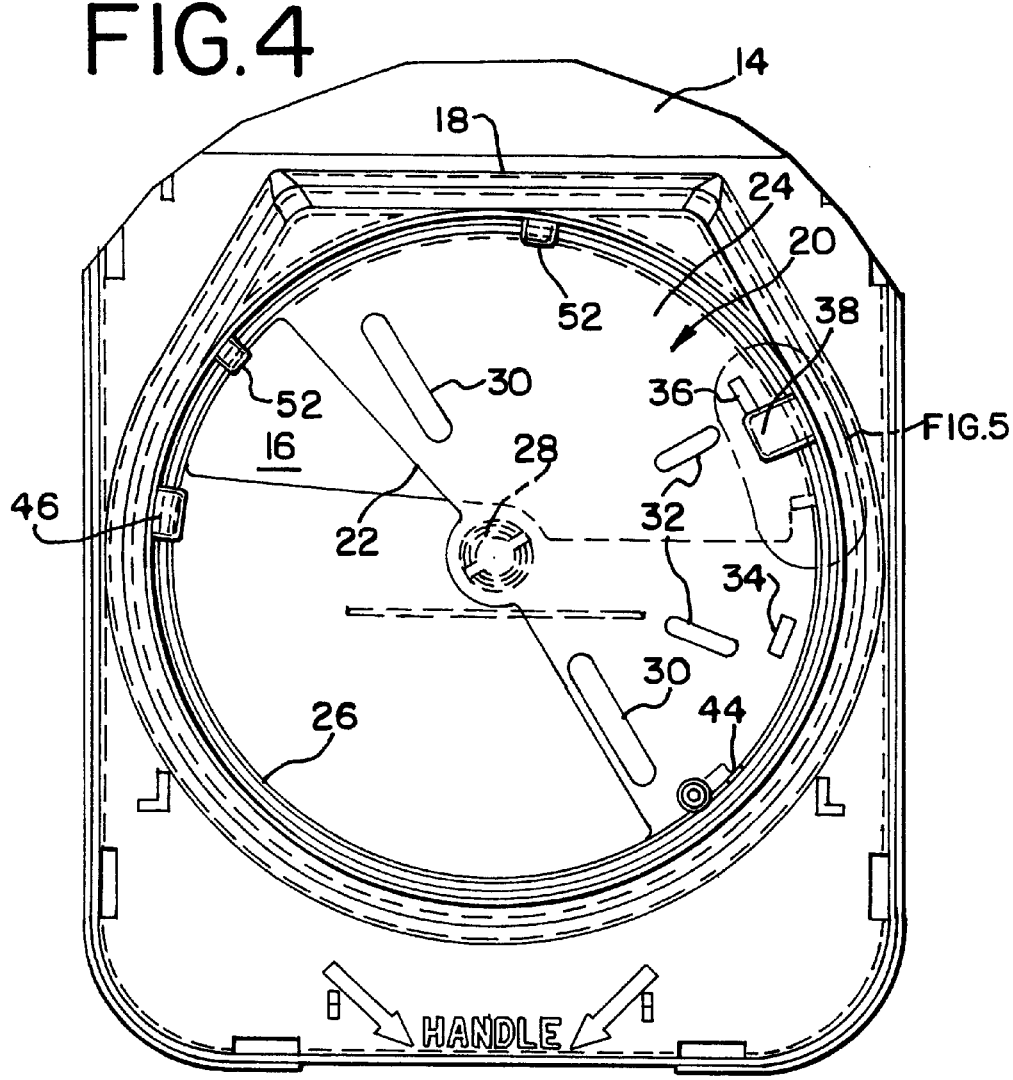
FIG. 4 is a partial top plan view of the lid as illustrated in FIG. 2, but with the rotary closure in an intermediate position with the disposal container partially opened to permit limited access to the interior.
Figure 5:
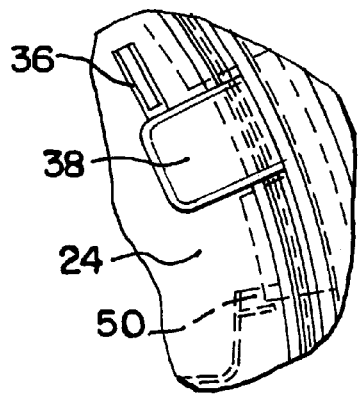
FIG. 5 is a further enlarged partial top plan view of a fragmentary portion of FIG. 4.

An intermediate position where the rotary closure 20 is partially closed is illustrated in FIG. 4. In this orientation, the nub 36 has been rotated beneath the control tab 38 so that the vertical wall 42 butts against the control tab 38. Thus, the rotary closure 20 cannot be rotated in the clockwise direction (in relation to FIG. 4) without either the tab 38 being displaced upwardly to permit the nub 36 to pass, or the structure of the rotary closure 20 adjacent to the nub 36 and grip 32 being pressed downwardly so that the nub 36 can pass beneath the control tab 38. Thus, the position shown in FIG. 4 is an intermediate position where only a small, pie-shaped opening into the interior of the container body 12 is permitted.

Figure 6:
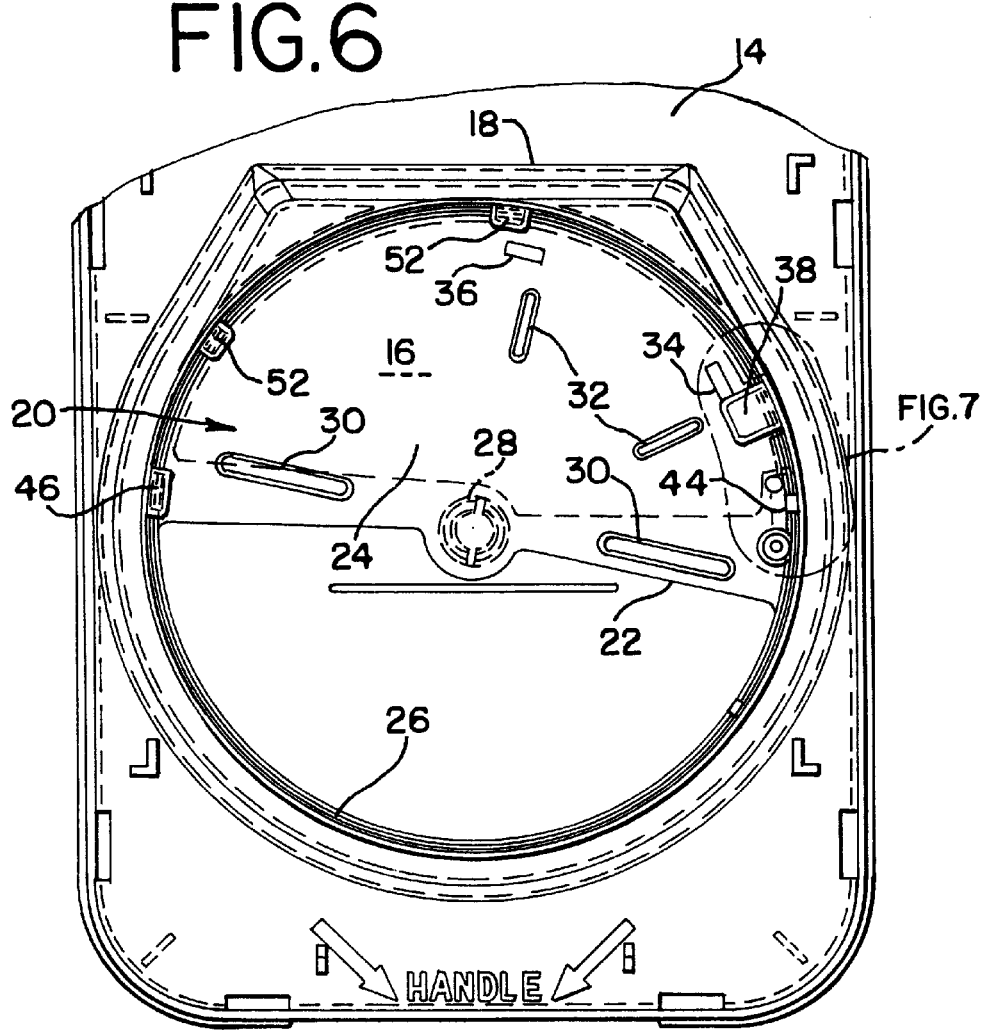
FIG. 6 is a partial top plan view similar to FIG. 2, but with the rotary closure in a temporarily closed position to temporarily prevent access to the interior of the container.
Figure 7:
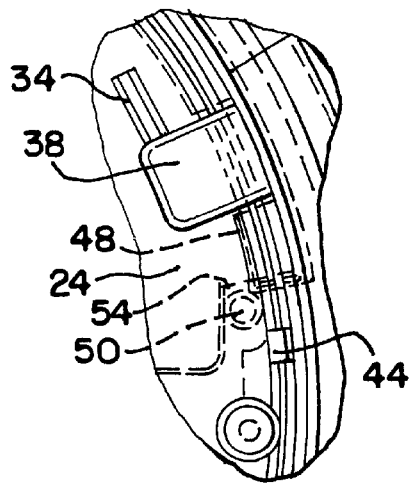
FIG. 7 is a further enlarged partial top plan view of a fragmentary portion of FIG. 6.

In FIG. 6, the rotary closure 20 has been rotated to a second intermediate position, where the container 10 is temporarily closed. In this orientation, the nub 34 has passed beneath the control tab 38 and has its upstanding vertical wall 42 butting against the control tab 38. Also, the first obstruction 48 has engaged the second obstruction 50 creating a frictional interface so that further rotation in the counterclockwise direction (in relation to FIG. 6) is inhibited, but not prevented.

Figure 8:
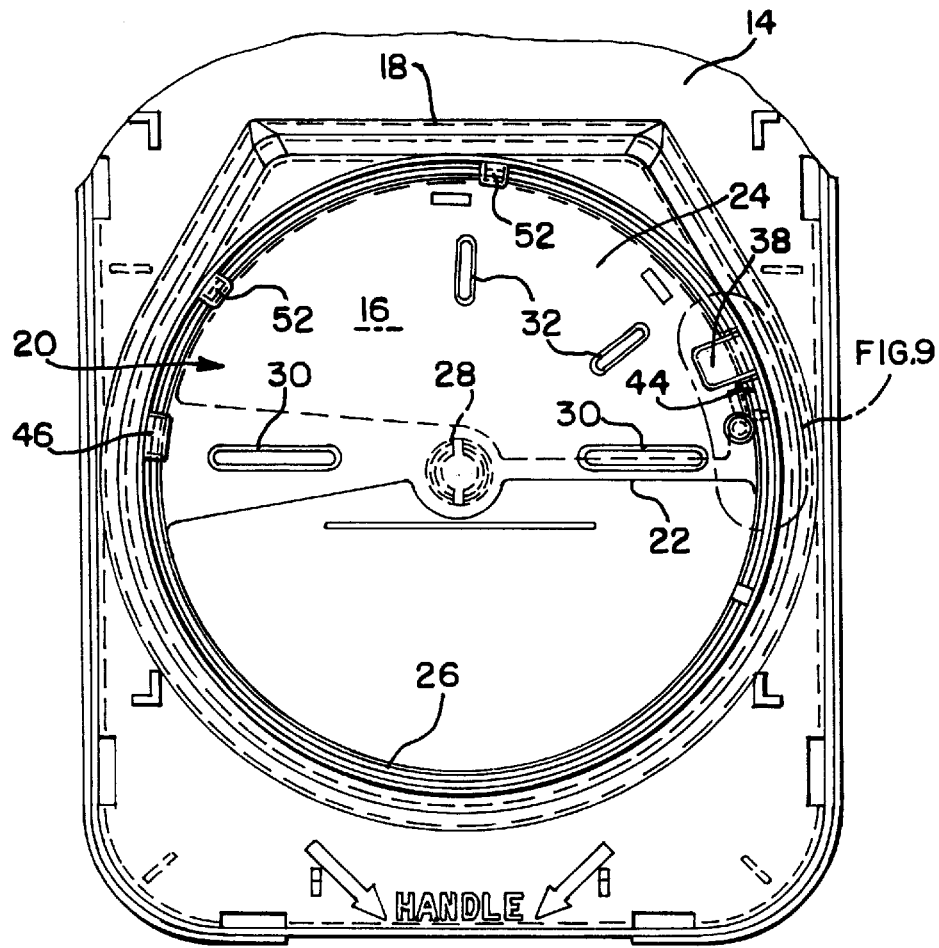
FIG. 8 is a partial top plan view similar to FIG. 2, but with the rotary closure in the locked position.
Figure 9:
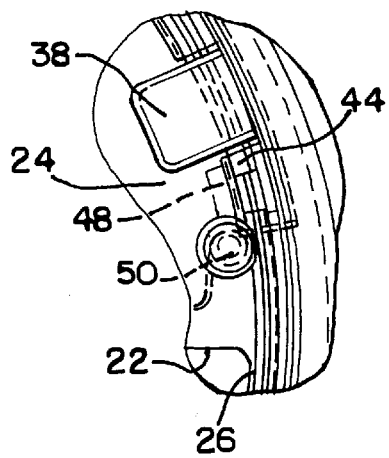
FIG. 9 is further enlarged partial top plan view of a fragmentary portion of FIG. 8.

In the orientation shown in FIG. 8, the rotary closure 20 has been rotated further to the locked position. In this orientation, the first obstruction 48 comprises a second stop and engages an abutment 54 in the lid 14 adjacent the access aperture 16. At the same time, the stop 44 is butted against the control tab 38. Therefore, the rotary closure 20 is locked in position and cannot be rotated in either the clockwise direction (because of the first obstruction engaging the abutment 54) or the counterclockwise direction (because of the stop 44 engaging the control tab 38). Access to the aperture 16, and therefore to the interior of the container body 12, is therefore prevented.

Various changes can be made to the invention without departing from the spirit thereof or scope of the following claims.

What is claimed is:

1. A disposal container, comprising
   a. a container body,
   b. a lid at the top of said container body,
   c. an access aperture in said lid, and
   d. a closure assembly shaped to overlie said access aperture, said closure assembly comprising
      i. a rotary closure having an open portion and a closed portion,
      ii. means for positioning said rotary closure in an open position with said open portion in registration with said aperture, permitting full access to said aperture,
      iii. means for positioning said rotary closure in a locked position with said closed portion in registration with said aperture, permanently preventing access to said aperture,
      iv. means for positioning said rotary closure in at least one intermediate position between said open position and said locked position with said rotary closure being temporarily prevented at said intermediate position from rotation toward one of said open and locked positions, and
      v. means for moving said rotary closure from said intermediate position by temporarily displacing a portion of said rotary closure relative to said lid to release said closure from said intermediate position.

2. A disposal container according to claim 1 including at least two of said intermediate positions, one of said intermediate positions comprising a partially open position permitting limited access to said aperture, and another of said intermediate positions comprising a temporarily closed position temporarily preventing access to said aperture.

3. A disposal container according to claim 2 in which said means for positioning said rotary closure at said partially open position comprises a control tab in said lid extending over said rotary closure and an upstanding nub on said rotary closure aligned to engage said control tab.

4. A disposal container according to claim 3 in which said nub includes an inclined shoulder to permit rotation of said rotary closure in one direction with said nub passing beneath said control tab.

5. A disposal container according to claim 3 in which said nub includes a vertical wall engaging said control tab to prevent rotation of said closure past said control tab.

6. A disposal container according to claim 2 in which said means for positioning said rotary closure at said temporarily closed position comprises a control tab in said lid over said rotary closure and an upstanding nub on said rotary closure aligned to engage said control tab.

7. A disposal container according to claim 6 in which said nub includes an inclined shoulder to permit rotation of said rotary closure in one direction with said nub passing beneath said control tab.

8. A disposal container according to claim 6 in which said nub includes a vertical wall engaging said control tab to prevent rotation of said closure past said control tab.

9. A disposal container according to claim 6 including means at said temporarily closed position for inhibiting rotation of said rotary closure to said locked position.

10. A disposal container according to claim 9 in which said means for inhibiting rotation comprises a first obstruction beneath said rotary closure engagable with a second obstruction formed in said lid.

11. A disposal container according to claim 10 in which at least one of said obstructions is frangible.

12. A disposal container according to claim 1 in which said means for positioning said rotary closure in at least one intermediate position comprises a control tab in said lid extending over said rotary closure and at least one nub on said rotary closure aligned to engage said control tab.

13. A disposal container according to claim 12 including at least two of said intermediate positions, one of said nubs being provided for each intermediate position.

14. A disposal container according to claim 1 in which said means for positioning said rotary closure in a locked position comprises a control tab in said lid extending over said closure and an upstanding stop on said rotary closure aligned to engage said control tab.

15. A disposal container according to claim 14 including a second stop on said rotary closure beneath said rotary closure engagable with an abutment in said lid adjacent said aperture, said upstanding stop engaging said control tab when said second stop engages said abutment.

16. A disposal container, comprising
   a. a container body,
   b. a lid at the top of said container body,
   c. an access aperture in said lid,
   d. a closure assembly shaped to overlie said access aperture, said closure assembly comprising
      i. a rotary closure having an open portion and a closed portion,
      ii. means for positioning said closure in a first open position with said open portion in registration with said aperture, permitting full access to said aperture,
      iii. means for positioning said closure in a second open position permitting limited access to said aperture,
      iv. means for positioning said closure in a first closed position temporarily preventing access to said aperture, and
      v. means for positioning said closure in a second closed portion with said closed portion in registration with said aperture, permanently preventing access to said aperture.

17. A disposal container according to claim 16 in which said means for positioning in a second open position comprises a control tab in said lid extending over said closure and an upstanding nub on said closure aligned to engage said control tab.

18. A disposal container according to claim 17 in which said nub includes an inclined shoulder to permit rotation of said closure in one direction with said nub passing beneath said control tab.

19. A disposal container according to claim 17 in which said nub includes a vertical wall engaging said control tab to prevent rotation of said closure past said control tab.

* * * * *